(12) United States Patent
Van Tilborg

(10) Patent No.: US 9,611,205 B2
(45) Date of Patent: *Apr. 4, 2017

(54) PHARMACEUTICAL COMPOUND FOR THE PREVENTION AND TREATMENT

(71) Applicant: Cesa Alliance S.A., Strassen (LU)

(72) Inventor: Reiner Van Tilborg, Strassen (LU)

(73) Assignee: Cesa Alliance S.A., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 15/069,118

(22) Filed: Mar. 14, 2016

(65) Prior Publication Data

US 2016/0194266 A1 Jul. 7, 2016

Related U.S. Application Data

(63) Continuation of application No. 14/758,343, filed as application No. PCT/EP2013/076936 on Dec. 17, 2013, now Pat. No. 9,284,250.

(30) Foreign Application Priority Data

Dec. 31, 2012 (LU) .......................... 92126

(51) Int. Cl.
| | | |
|---|---|---|
| *A01N 31/00* | (2006.01) | |
| *A61K 31/11* | (2006.01) | |
| *C07C 47/46* | (2006.01) | |
| *A61K 47/44* | (2017.01) | |
| *A61K 9/00* | (2006.01) | |
| *A61K 49/04* | (2006.01) | |
| *A61K 51/04* | (2006.01) | |

(52) U.S. Cl.
CPC ............ *C07C 47/46* (2013.01); *A61K 9/0095* (2013.01); *A61K 31/11* (2013.01); *A61K 47/44* (2013.01); *A61K 49/0433* (2013.01); *A61K 51/04* (2013.01); *C07C 2101/16* (2013.01)

(58) Field of Classification Search
CPC ...... A61K 31/11; A61K 47/44; A61K 9/0095; C07C 2101/16; C07C 47/46
See application file for complete search history.

(56) References Cited

FOREIGN PATENT DOCUMENTS

WO 0168576 A1 9/2001

OTHER PUBLICATIONS

STN Accession No. 1998:446875, 1998.*
Ito et al. Cancer Science 2003, 94, 3-8.*
International Search Report for PCT/EP2013/076936 dated Jan. 21, 2014.

* cited by examiner

*Primary Examiner* — Jean Cornet
(74) *Attorney, Agent, or Firm* — Fish & Tsang LLP

(57) ABSTRACT

Contemplated compounds, compositions, and methods are presented for use in the treatment, or prevention, of a cognitive, neurodegenerative or neuronal disorder or disease, such as Alzheimer's disease.

10 Claims, 7 Drawing Sheets

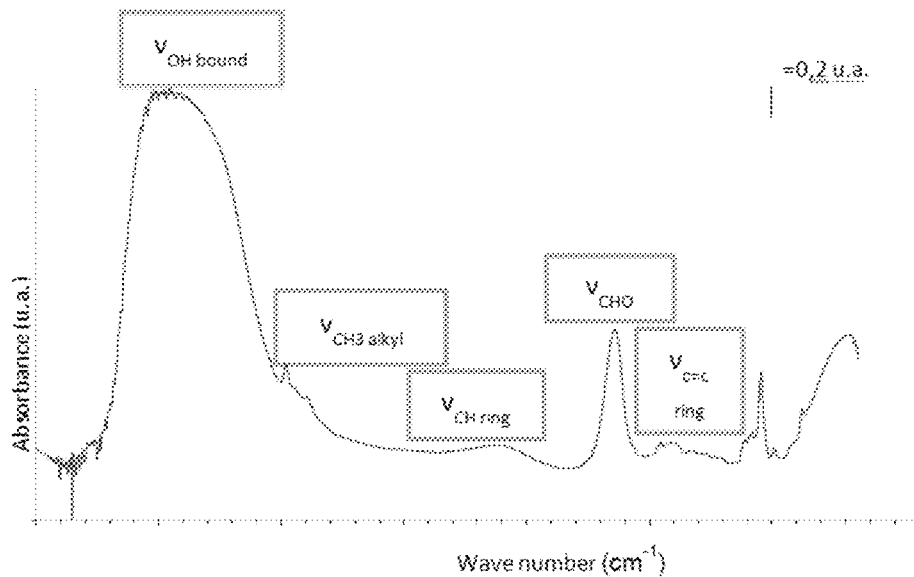
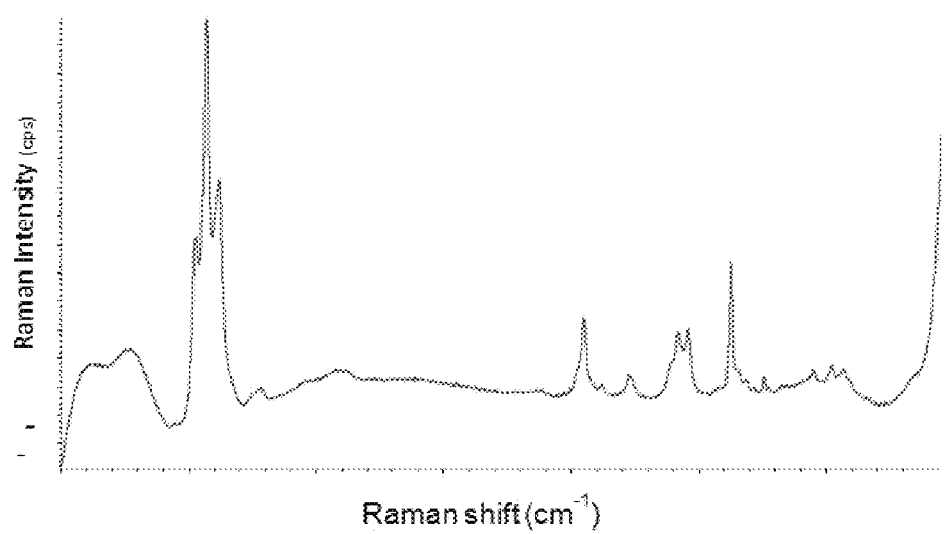
Figure 1C

Mini – Mental State Examination

Instructions: Score one point for each correct respons with each question or activity Patient's Name : JH01
Date :

| | Maximum score | Base | 3 months | 6 months |
|---|---|---|---|---|
| Orientation Time | | | | |
| 1. What is the year | 1 | 0 | 0 | 0 |
| 2. What is the season | 1 | 0 | 0 | 0 |
| 3. What is the month | 1 | 0 | 0 | 0 |
| 4. What is the date | 1 | 0 | 0 | 0 |
| 5. Which day of the week is it | 1 | 0 | 0 | 0 |
| Orientation Place | | | | |
| 1. In which province are we now | 1 | 0 | 0 | 0 |
| 2. In which town are we now | 1 | 0 | 1 | 1 |
| 3. Where are we now (hospital/ home) | 1 | 0 | 1 | 1 |
| 4. In what street are we now | 1 | 0 | 0 | 0 |
| 5. On which floor/in which number are we now | 1 | 0 | 0 | 0 |
| Registration | | | | |
| The examiner names 3 unrelated objects (eg apple-key-table) clearly and slowly, then the instructor asks for the patient to name all 3 of them. The patient's response is used for scoring. The words can be repeated afterwords (max 5 times) until patients knows all 3 | 3 | 1 | 1 | 2 |
| Concentration | | | | |
| "I would like you to count backward from 100 by sevens." (93, 86, 79, 72, 65, ...) Alternative: "Spell the word WORLD backwards." (D-L-R-O-W) Maximum time given : 1 minute and 5 calculations | 5 | 0 | 0 | 0 |
| Memory | | | | |
| "Earlier I told you the names of three things. Can you tell me what those were?" | 3 | 0 | 0 | 1 |
| Naming | | | | |
| Show the patient 2 simple objects, such as a wristwatch and a pen and ask the patient to name them | 2 | 1 | 2 | 2 |
| Repetition | | | | |
| "Repeat the phrase: No ifs, ands or buts." | 1 | 0 | 1 | 1 |
| Comprehension | | | | |
| "Take the paper in your right hand, fold it in half and put it on the floor (The examiner gives the patient a piece of blank paper.) | 3 | 0 | 0 | 3 |
| Reading | | | | |
| "Please read this and do what it says." (Written Instruction is "Close your eyes.") | 1 | 0 | 1 | 1 |
| Writing | | | | |
| "Make up a sentence about anything." (This sentence must contain a noun and a verb) | 1 | 0 | 1 | 1 |
| Drawing | | | | |
| "Please copy this picture." All 10 angles must be present and two must intersect | 1 | 0 | 0 | 0 |

Folstein MF, Folstein SE, McHugh PR: "Mini-mental state: A practical method for grading the cognitive state of patients for the clinician." J Psychiatr Res 1975;12:189-198.

Figure 2

The Barthel Index

Instructions: score 0, 5, 10 or 15 points depending on patients abilities

Patient's Name: Observational Study AA7 - Test Subject AA7-03

| | Max score | Base | 6 Month | +/- |
|---|---|---|---|---|
| 1. Feeding | | | | |
| Independent | 10 | | | |
| Needs help cutting, spreading butter, etc., or requires modified diet | 5 | 5 | 10 | |
| Unable | 0 | | | |
| 2. Bathing | | | | |
| Independent (or in shower) | 5 | 0 | 5 | |
| Dependent | 0 | | | |
| 3. Grooming | | | | |
| Independent face/hair/teeth/shaving (implements provided) | 5 | 0 | 5 | |
| Needs help with personal care | 0 | | | |
| 4. Dressing | | | | |
| Independent (includes buttons, zips, laces, etc.) | 10 | | | |
| Needs help but can do about half unaided | 5 | 5 | 10 | |
| Dependent | 0 | | | |
| 5. Bowels | | | | |
| Continent | 10 | | | |
| Occasional accident | 5 | 5 | 10 | |
| Incontinent (or needs to be given enemas) | 0 | | | |
| 6. Bladder | | | | |
| Continent | 10 | | | |
| Occasional accident | 5 | 5 | 10 | |
| Incontinent, or cathetherized and unable to manage alone | 0 | | | |
| 7. Toilet Use | | | | |
| Independent (on and off, dressing, wiping) | 10 | | | |
| Needs some help but can do something alone | 5 | 5 | 10 | |
| Dependent | 0 | | | |
| 8. Transfers (bed to chair and back) | | | | |
| Independent | 15 | | | |
| Minor help (verbal or physical) | 10 | 10 | 15 | |
| Major help (one or two people, physical), can sit | 5 | | | |
| Unable, no sitting balance | 0 | | | |
| 9. Mobility (on level surfaces) | | | | |
| Independent (but may use any aid, eg stick) > 50 meters | 15 | | | |
| Walks with help of one person (verbal or physical) > 50 meters | 10 | 10 | 15 | |
| Wheelchair dependent including corners, >50 meters | 5 | | | |
| Immobile or < 50 meters | 0 | | | |
| 10. Stairs | | | | |
| Independent | 10 | | | |
| Needs help (verbal, physical, carrying aid) | 5 | 5 | 10 | |
| Unable | 0 | | | |
| Total Score | 0-100 | 50 | 100 | 50 |

Figure 3

Mini - Mental State Examination (MMSE)

Instructions: Score one point for each correct respons witin each question or activity

Patient: Observational Study AA7 - Test Subject AA7-03

| | Max score | Base | 6 Months | +/- |
|---|---|---|---|---|
| Orientation Time | | | | |
| 1. What is the year | 1 | 0 | 0 | |
| 2. What is the season | 1 | 0 | 0 | |
| 3. What is the month | 1 | 0 | 0 | |
| 4. What is the date | 1 | 0 | 0 | |
| 5. Which day of the week is it | 1 | 0 | 0 | |
| Orientation in Place | | | | |
| 1. In which province are we now | 1 | 0 | 0 | |
| 2. In which town are we now | 1 | 1 | 1 | |
| 3. Where are we now (hospital/ home) | 1 | 1 | 1 | |
| 4. In what street are we now | 1 | 0 | 1 | |
| 5. On which floor/in which number are we now | 1 | 0 | 0 | |
| Memory | | | | |
| The examiner names 3 unrelated objects (eg apple-key-table) clearly and slowly, then the instructor asks for the patient to name all 3 of them. The patient's response is used for scoring. The words can be repeated afterwords (max 5 times) until patients knows all 3 | 3 | 1 | 2 | |
| Concentration | | | | |
| "I would like you to count backward from 100 by sevens." (93, 86, 79, 72, 65, ...) Alternative: "Spell the word WORLD backwards." (D-L-R-O-W) Maximum time given : 1 minute and 5 calculations | 5 | 0 | 1 | |
| Memory 2 | | | | |
| "Earlier I told you the names of three things. Can you tell me what those were?" | 3 | 0 | 1 | |
| Language | | | | |
| Show the patient 2 simple objects, such as a wristwatch and a pen and ask the patient to name them | 2 | 2 | 2 | |
| Language 2 | | | | |
| "Repeat the phrase: No ifs, ands or buts." | 1 | 0 | 1 | |
| Language 3 | | | | |
| "Take the paper in your right hand, fold it in half and put it on the floor (The examiner gives the patient a piece of blank paper.) | 3 | 0 | 3 | |
| Language 4 | | | | |
| "Please read this and do what it says." (Written instruction is "Close your eyes.") | 1 | 0 | 1 | |
| Language 5 | | | | |
| "Make up a sentence about anything." (This sentence must contain a noun and a verb | 1 | 1 | 1 | |
| Language 6 | | | | |
| "Please copy this picture." All 10 angles must be present and two must intersect | 1 | 0 | 0 | |
| Total Score | 30 | 6 | 15 | |

Figure 4

| Q | Action/Subject | 2 Pnt | S/A | Total | Control Group | | | Placebo | | | Active- A7:RVT | | |
|---|---|---|---|---|---|---|---|---|---|---|---|---|---|
| | | | | | C00 | C30 | C60 | P00 | P30 | P60 | A00 | A30 | A60 |
| 1 | Trip | 1 | 2 | 4 | 4 | 4 | 4 | 1 | 2 | 1 | 2 | 2 | 4 |
| 2 | Names | 2 | 2 | 8 | 8 | 8 | 8 | 0 | 0 | 1 | 1 | 2 | 4 |
| 3 | Cities | 2 | 2 | 8 | 8 | 8 | 8 | 2 | 1 | 1 | 2 | 2 | 4 |
| 4 | Incident | 1 | 2 | 4 | 4 | 4 | 4 | 2 | 0 | 0 | 1 | 1 | 3 |
| 5 | Number of Cars | 1 | 2 | 4 | 4 | 4 | 4 | 0 | 0 | 0 | 0 | 1 | 2 |
| 6 | Color Car | 1 | 2 | 4 | 4 | 4 | 4 | 0 | 0 | 0 | 0 | 0 | 3 |
| 7 | Hotel | 1 | 2 | 4 | 2 | 4 | 4 | 0 | 0 | 0 | 0 | 0 | 0 |
| 8 | Walk city | 1 | 2 | 4 | 4 | 4 | 4 | 0 | 0 | 0 | 0 | 0 | 0 |
| 9 | Fountain | 1 | 2 | 4 | 4 | 4 | 4 | 0 | 0 | 0 | 0 | 1 | 3 |
| 10 | Coins | 1 | 2 | 4 | 4 | 4 | 4 | 0 | 0 | 0 | 0 | 0 | 0 |
| 11 | Number Coins | 1 | 2 | 4 | 3 | 4 | 4 | 0 | 0 | 0 | 0 | 0 | 0 |
| 12 | Diner | 1 | 2 | 4 | 4 | 4 | 4 | 0 | 0 | 0 | 0 | 0 | 0 |
| 13 | Courses | 1 | 2 | 4 | 4 | 4 | 4 | 0 | 0 | 0 | 0 | 0 | 3 |
| 14 | Piano bar | 1 | 2 | 4 | 4 | 4 | 4 | 0 | 0 | 0 | 0 | 0 | 0 |
| 15 | Favorite tune | 2 | 2 | 8 | 2 | 4 | 8 | 0 | 0 | 0 | 0 | 0 | 0 |
| 16 | Morning | 1 | 2 | 4 | 4 | 4 | 4 | 0 | 0 | 0 | 0 | 0 | 0 |
| 17 | Hospital | 1 | 2 | 4 | 3 | 2 | 4 | 0 | 0 | 0 | 0 | 0 | 2 |
| 18 | Name Aunt | 2 | 2 | 8 | 4 | 4 | 8 | 0 | 0 | 0 | 0 | 0 | 0 |
| 19 | Disease | 2 | 2 | 8 | 8 | 8 | 8 | 0 | 0 | 0 | 0 | 0 | 0 |
| 20 | Present | 1 | 2 | 4 | 4 | 4 | 4 | 0 | 0 | 0 | 0 | 0 | 0 |
| | | 25 | | 100 | 86 | 90 | 100 | 5 | 3 | 3 | 6 | 9 | 28 |
| | | | | | 276 | | | 11 | | | 43 | | |

Figure 5

PHARMACEUTICAL COMPOUND FOR THE PREVENTION AND TREATMENT

This application is a continuation of allowed U.S. patent application Ser. No. 14/758,343 filed on Jun. 29, 2015, which is a national stage of PCT/EP2013/076936 filed on Dec. 17, 2013, which claims priority to Luxembourg Patent Application No. 92126 filed on Dec. 31, 2012. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

FIELD OF THE INVENTION

The present invention relates to compounds and compositions that may be used for preventing or treating cognitive, neurodegenerative or neuronal disorder or diseases.

BACKGROUND

Alzheimer's disease (also referred to as "AD") is the most common form of dementia. Most often, it is diagnosed in people over 65 years of age, although the less-prevalent early-onset Alzheimer's can occur much earlier. In 2006, there were 26.6 million sufferers worldwide. Alzheimer's is predicted to affect 1 in 85 people globally by 2050. The earliest observable symptoms are often mistakenly thought to be 'age-related' concerns, or manifestations of stress. In the early stages, the most commonly recognized symptom is inability to acquire new memories, such as difficulty in recalling recently observed facts.

As the disease advances, gradually, bodily functions are lost, ultimately leading to death. Individual prognosis is difficult to assess, as the duration of the disease varies. AD develops for an indeterminate period of time before becoming fully apparent, and it can progress undiagnosed for years. The mean life expectancy following stage 2 diagnosis is approximately seven years. Fewer than three percent of individuals live more than fourteen years after diagnosis. In developed countries, AD is one of the most costly diseases to society.

A 2004 study tried to explain the causes of the AD and found that deposition of amyloid plaques does not correlate well with neuron loss. This observation supports the tau hypothesis, the idea that tau protein abnormalities initiate the disease cascade.

Another cause, on which most currently available drug therapies are based, is the cholinergic hypothesis, which proposes that AD is caused by reduced synthesis of the neurotransmitter acetylcholine. The cholinergic hypothesis has not maintained widespread support, largely because medications intended to treat acetylcholine deficiency have not been very effective. Other cholinergic effects have also been proposed, for example, initiation of large-scale aggregation of amyloid, leading to generalized neuroinflammation.

Four medications are currently approved by regulatory agencies such as the U.S. Food and Drug Administration (FDA) and the European Medicines Agency (EMA) to treat the cognitive manifestations of AD: three are acetylcholinesterase inhibitors and the other is memantine, an NMDA receptor antagonist. No drug has an indication for delaying or halting the progression of the disease.

At present, there is no definitive evidence to support that any particular measure is effective in preventing AD. The journal "Food chemistry" 116 (2009), pages 470 to 479, relates to the antioxidant, anticholinesterase and antimicrobial constituents from the essential oil and ethanol extract of *Salvia potentillifolia*. The journal "Food chemistry" 108 (2008), pages 663 to 668, relates to the inhibitory effect of Turkish *Rosmarinus officinalis* L. on acetylcholinesterase and butyrylcholinesterase enzymes.

WO 01/68576 relates to dermatological compounds, i.e. novel monocyclic and bicyclic monoterpene diols that stimulate melanogenesis in mammalian skin, hair, wool or fur, and, are useful for treating or preventing various skin and proliferative disorders, neurodegenerative diseases, and diseases regulated by the nitric oxide/cyclic GMP/protein kinase G pathway. WO 01/68576 discloses monoterpenes as pharmaceutically active compounds. The background description includes information that may be useful in understanding the present invention. It is not an admission that any of the information provided herein is prior art or relevant to the presently claimed invention, or that any publication specifically or implicitly referenced is prior art.

Thus, there is still a need to explore and provide further compositions and methods for treating cognitive diseases.

SUMMARY OF THE INVENTION

The inventive subject matter provides various compounds, compositions, and methods that are useful in the prevention or treatment of a cognitive, neurodegenerative or neuronal disorder or disease. More particularly, the compounds, compositions, and methods described herein are effective in the treatment and prevention Alzheimer's disease.

In one aspect of the inventive subject matter, a contemplated compound has a structure according to Formula A

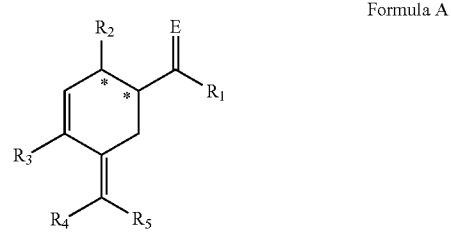

Formula A wherein $R_1$, $R_2$, $R_3$, $R_4$, and $R_5$ are independently hydrogen, lower alkyl, hydroxyl, amino, alkyl amino, or optionally substituted $C_1$-$C_8$ alkyl, optionally labeled with a PET- or SPECT detectable label, and E is O or S.

In preferred embodiments, $R_1$ is a hydrogen or lower alkyl, $R_2$ is lower alkyl, $R_3$ is OH or SH, and $R_4$ and $R_5$ are lower alkyl. For example, a contemplated compound has a structure according to Formula 1

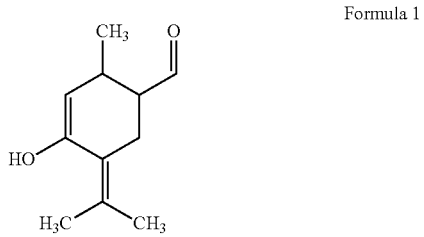

Formula 1

In some aspects, contemplated compounds comprise a mixture of stereoisomers. For example, the compound can be a mixture of two or three from the group consisting of

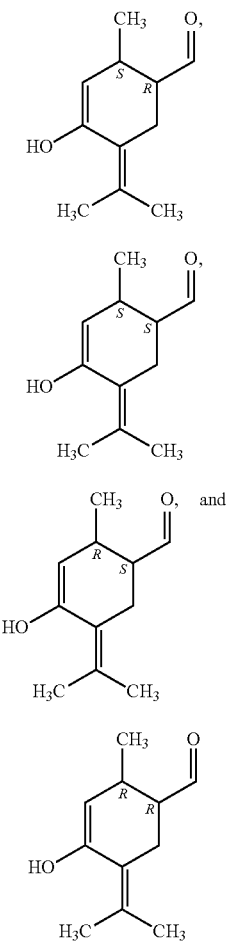

Formula 2

Formula 3

Formula 4

Formula 5

However, in other contemplated aspects, the compound can be an isolated stereoisomer.

In another aspect of the inventive subject matter, a pharmaceutical composition for treatment of a condition associated with a cognitive, neurodegenerative or neuronal disorder or disease is contemplated comprising a compound according to Formula A, and a pharmaceutically acceptable carrier. Most preferably, the compound is present in an amount effective to treat or prevent a condition associated with a cognitive, neurodegenerative or neuronal disorder or disease. In some aspects, the pharmaceutical composition can comprise a compound according to Formula 1, and a pharmaceutically acceptable carrier. The compound can be a mixture of stereoisomers (e.g., Formulas 2-5) or an isolated stereoisomer.

The inventor also contemplates use of a compound according to Formula A in the manufacture of a medicament for treatment or prevention of a condition associated with a cognitive, neurodegenerative or neuronal disorder or disease. Most typically, the condition includes at least one of dementias such as Alzheimer's disease, memory loss, attention deficit symptoms associated with Alzheimer's disease, diffuse Lewy body type Alzheimer's disease, mild cognitive impairment, Hereditary Cerebral Haemorrhage with Amyloidosis of the Dutch-Type, [beta]-amyloid angiopathy and cerebral bleeding such as cerebral bleeding due to solitary cerebral amyloid angiopathy, prion infections, degenerative dementias, including dementias of mixed vascular and degenerative origin, frontotemporal dementia, pre-senile dementia, senile dementia, parkinsonian disorders such as Parkinson's disease (PD), subacute sclerosing panencephalitic parkinsonism, postencephalitic parkinsonism, pugilistic encephalitis, guam parkinsonism-dementia complex, Pick's disease, multiple system atrophy (MSA), progressive supranuclear palsy (PSP), and corticobasal degeneration (CBD), Down syndrome, Lewy body disease, Huntington's Disease, amyotrophic lateral sclerosis, multiple sclerosis and neurotraumatic diseases such as acute stroke, epilepsy, promotion of functional recovery post stroke, ischaemia, brain injury, especially traumatic brain injury and neuroinflammation.

In a still further aspect, the inventor also contemplates a method of treating, or preventing, a condition associated with a cognitive, neurodegenerative or neuronal disorder or disease that includes a step of administering a pharmaceutical composition comprising a compound according to Formula A at a concentration effective to treat or prevent the condition associate with a cognitive, neurodegenerative or neuronal disorder or disease.

In yet another aspect, the inventor contemplates a method of imaging a cognitive, neurodegenerative or neuronal disorder or disease in a subject, comprising administering to the subject a diagnostic composition comprising a compound according to Formula A and a PET- or SPECT detectable label.

Various objects, features, aspects and advantages of the inventive subject matter will become more apparent from the following detailed description of embodiments, along with the accompanying drawing figures in which like numerals represent like components.

BRIEF DESCRIPTION OF THE DRAWINGS

FIG. 1C are infrared and Raman spectroscopies of the (1R,2R) and (1S,2S) trans isomers of Formula 1.

FIG. 2 is a Mini-Mental State Examination of Patient JH01.

FIG. 3 is a Barthel Index of Patient AA7-003.

FIG. 4 is a Mini-Mental State Examination of Patient AA7-003.

FIG. 5 is a Short term Memory Recovery Test of the subjects in Experimental Data 3.

DETAILED DESCRIPTION

Figure 1A:
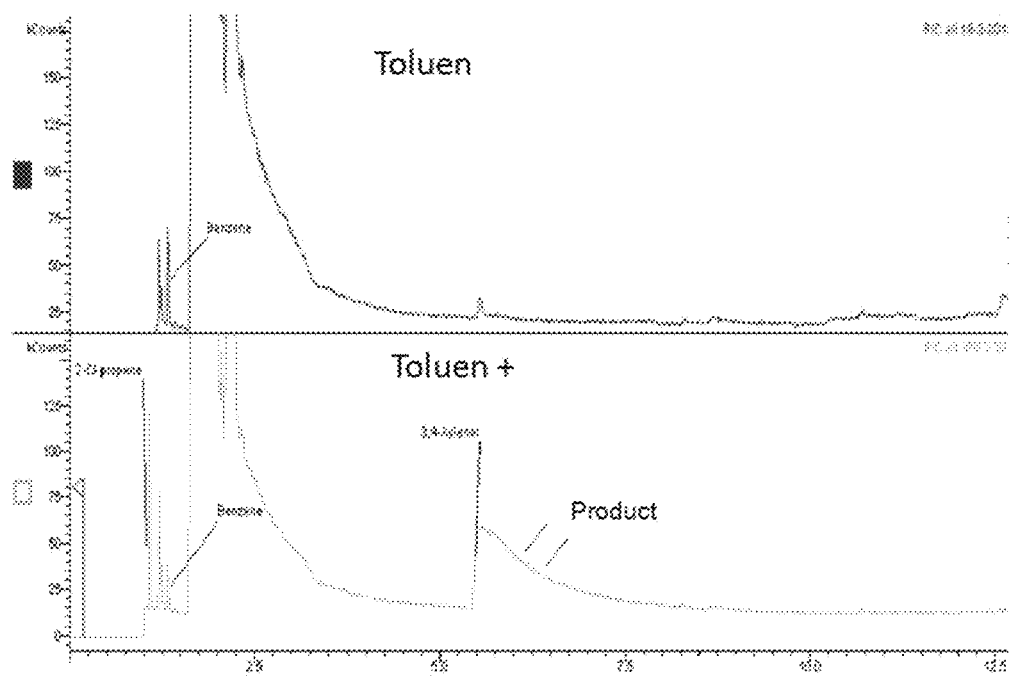
FIG. 1A is a mass spectroscopy analysis of the final mixture of the exemplary synthesis.

The inventor has surprisingly discovered that cognitive, neurodegenerative or neuronal disorders or diseases can be treated or prevented using contemplated compounds, compositions, and methods described herein. For example, contemplated compounds and compositions have been found to reduce the severity of Alzheimer's disease from stage 6 to stage 4 or less. Thus, contemplated compounds and compositions may be used for all conditions and/or disorders that are associated with cognitive, neurodegenerative or neuronal disorders or diseases.

Contemplated Compounds

In one aspect of the inventive subject matter, contemplated compounds have a structure according to Formula A

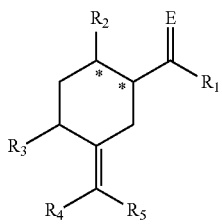

Formula A where E is oxygen, S, NH or $CH_2$, and $R_1$, $R_2$, $R_3$, $R_4$, $R_5$ are independently hydrogen, halogen, hydroxyl, amino, alkylamino ($C_{1-6}$, linear, branched, or cyclic ($C_{3-6}$)) or optionally substituted $C_{1-8}$ alkyl (e.g., substituted with hydroxyl, halogen, nitro, hydrosulfide, amino, etc.), optionally labeled with a PET- or SPECT detectable label. In contemplated aspects, $R_1$ is hydrogen, $R_2$, $R_4$, $R_5$ are independently methyl groups, $R_3$ is a hydroxyl group and E is oxygen.

The term "substituted" as used herein refers to a replacement of an atom or chemical group (e.g., H, $NH_2$, or OH) with a functional group, and particularly contemplated functional groups include nucleophilic groups (e.g., $-NH_2$, $-OH$, SH, $-NC$, etc.), electrophilic groups (e.g., C(O)OR, C(X)OH, etc.), polar groups (e.g., $-OH$), non-polar groups (e.g., aryl, alkyl, alkenyl, alkynyl, etc.), ionic groups (e.g., $NH_3^+$), and halogens (e.g., $-F$, $-Cl$), and all chemically reasonable combinations thereof. Thus, the term "functional group" as used herein refers to a nucleophilic group (e.g., $-NH_2$, $-OH$, SH, $-NC$, $-CN$ etc.), an electrophilic group (e.g., C(O)OR, C(X)OH, C(Halogen)OR, etc.), a polar group (e.g., $-OH$), a non-polar group (e.g., aryl, alkyl, alkenyl, alkynyl, etc.), an ionic group (e.g., $NH_3^+$), and a halogen.

In preferred aspects, E is a oxygen or S, $R_1$ is hydrogen or a lower alkyl ($C_1$-$C_3$), $R_2$, $R_4$, $R_5$ are independently a lower alkyl ($C_1$-$C_3$), and $R_3$ is OH or SH. Most typically, contemplated compounds comprise a structure according to Formula 1

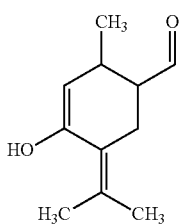

Formula 1

However, it should be noted that further alternatives are contemplated, including bioisosteric replacements of the radicals in $R_1$-$R_5$ (e.g., Bioisosterism: A Rational Approach in Drug Design, Patani et al., Chem. Rev. 1996, 96, 3147-3176).

It should be appreciated that contemplated compounds can comprise a mixture of stereoisomers. For example, a compound can be a mixture of all the stereoisomers produced. In another example, the compounds can be a mixture of two stereoisomers or a mixture of three stereoisomers. It is also contemplated that the compound is a single stereoisomer. Thus, various stereoisomers are contemplated as shown below:

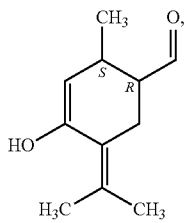

Formula 2

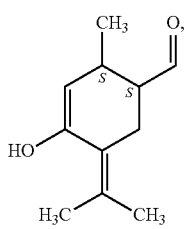

Formula 3

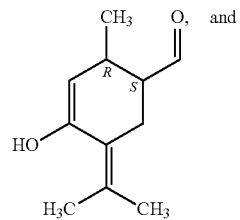

Formula 4

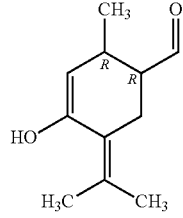

Formula 5

Certain compounds contemplated herein may comprise one or more asymmetric centers, and therefore exist in different enantiomeric forms as shown above. It should be recognized that all enantiomeric forms of contemplated compounds are specifically contemplated herein. Similarly, where contemplated compounds exhibit optical activity and/or have stereoisomers, all isomeric forms are contemplated herein. Furthermore, where double bonds distinguish a Z-form from an E-form (or cis- from trans-), both isomers are contemplated.

Still further, it should be recognized that the compounds according to the inventive subject matter may also be isotopically-labeled. Examples of suitable isotopes $^2H$, $^3H$, $^{11}C$, $^{13}C$, $^{14}C$, $^{15}N$, $^{18}O$, $^{17}O$, $^{18}F$, or $^{36}Cl$. Most preferably, where the compounds are used for diagnostics, compounds according to the inventive subject matter will be labeled, typically with a PET- or SPECT detectable label. Most preferred labels include $^{18}F$ and $^{11}C$.

Contemplated compounds may be prepared as pharmaceutically acceptable salt(s), which especially include salts of acidic or basic groups which may be present in the contemplated compounds. For example, contemplated compounds that are basic in nature may form a wide variety of salts with various inorganic and organic acids. Suitable acids will provide pharmacologically acceptable anions, including chloride, bromide, iodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate [1,1'-methylene-bis-(2-hydroxy-3-naphthoate)] anions. Similarly, compounds that are acidic in nature may form base salts with various pharmacologically acceptable cations, and especially suitable cations include alkali metal or alkaline earth metal ions (e.g., sodium and potassium cations).

It should further be recognized that the compounds contemplated herein may also be active and/or prepared as a metabolites, as prodrugs, and/or otherwise modified compound, wherein the metabolite, prodrug, or modified compound exhibits higher permeability across the blood brain barrier or less toxicity as compared to the unmodified compound and wherein the prodrug or modified compound is converted within the target cell/organ/structure back into the unmodified form. For example, conversion of contemplated compounds into prodrugs may be useful where the active drug is too toxic for safe systemic administration, or where the contemplated compound is less rapidly transported across the blood brain barrier, or where the body breaks down the compound before reaching its target. Contemplated compounds may also be transformed by the hepatic phase I and/or phase II enzyme system, or by gastric acidity, intestinal microbial environment, or other biochemical process. Thus, suitable compounds may be oxidized, hydroxylated, ligated to a carbohydrate, etc. Similarly, contemplated compounds may be formulated such as to facilitate transport across the blood brain barrier, and all known formulations are deemed suitable for use herein.

Contemplated Pharmaceutical Compositions

Based on the inventor's discovery of biological activity of contemplated compounds, it is generally contemplated that the compounds according to the inventive subject matter may be formulated for treatment or prevention of various diseases associated with cognitive, neurodegenerative or neuronal disorders or diseases. Therefore, and among other contemplated uses, the inventor especially contemplates that pharmaceutical compositions comprising contemplated compounds may be effective for the treatment or prevention cognitive, neurodegenerative or neuronal disorders or diseases wherein contemplated pharmaceutical compositions comprise a therapeutically effective amount of contemplated compounds (or pharmaceutically acceptable salt, hydrate, or prodrug thereof), and a pharmaceutically acceptable carrier.

For example, in one aspect of the inventive subject matter, a pharmaceutical composition comprises a compound according to Formula A, or a pharmaceutically acceptable salt thereof, for use in the prevention or treatment of a cognitive, neurodegenerative or neuronal disorder or disease, such as Alzheimer's disease is contemplated. In contemplated compositions, the compound can be according to Formula 1 or a pharmaceutically acceptable salt thereof. Furthermore, the compound can be a mixture of stereoisomers (see Formulas 2-5) or an isolated stereoisomer.

The cognitive, neurodegenerative or neuronal disorder or disease of the compound of the present invention is selected from at least one of: chronic neurodegenerative conditions including dementias such as Alzheimer's disease, memory loss, attention deficit symptoms associated with Alzheimer's disease, diffuse Lewy body type Alzheimer's disease, mild cognitive impairment, Hereditary Cerebral Haemorrhage with Amyloidosis of the Dutch-Type, [beta]-amyloid angiopathy and cerebral bleeding such as cerebral bleeding due to solitary cerebral amyloid angiopathy, prion infections, degenerative dementias, including dementias of mixed vascular and degenerative origin, frontotemporal dementia, pre-senile dementia, senile dementia, AIDS associated dementia, parkinsonian disorders such as Parkinson's disease (PD), subacute sclerosing panencephalitic parkinsonism, postencephalitic parkinsonism, pugilistic encephalitis, guam parkinsonism-dementia complex, Pick's disease, multiple system atrophy (MSA), progressive supranuclear palsy (PSP), and corticobasal degeneration (CBD), Down syndrome, Lewy body disease, Huntington's Disease, amyotrophic lateral sclerosis, multiple sclerosis and neurotraumatic diseases such as acute stroke, epilepsy, promotion of functional recovery post stroke, ischaemia, brain injury, especially traumatic brain injury and neuroinflammation.

In most cases, the pharmaceutical composition of the present invention comprises a pharmaceutically acceptable carrier suitable for injection, oral administration, or other parenteral route. The pharmaceutically acceptable carrier is preferably a lipophilic carrier, such as a base oil. Suitable base oils include acai oil, almond oil, amaranth oil, apple seed oil, apricot oil, argan oil, artichoke oil, avocado oil, babassu oil, ben oil, blackcurrant seed oil, borage seed oil, borneo tallow nut oil, bottle gourd oil, buffalo gourd oil, butternut squash seed oil, cape chestnut oil, carob pod oil, carob seed pods oil, cashew oil, cassia oil, castor oil, cocklebur oil, cocoa butter, coconut oil, cohune oil, coriander seed oil, corn oil, cotton seed oil, dika oil, evening primrose oil, false flax oil, flax seed oil, grape seed oil, hazelnut oil, hemp oil, kapok seed oil, kenaf Seed oil, lallemantia oil, macadamia oil, manila oil, meadowfoam seed oil, mongongo nut oil (or manketti oil), mustard oil, nutmeg butter, oils from melon and gourd seeds, okra seed oil, olive oil, palm oil, papaya oil, peanut oil, pecan oil, pequi oil, perilla seed oil, pine nut oil, pine nut oil, pistachio oil, poppyseed oil, prune kernel oil, pumpkin seed oil, quinoa oil, radish oil, ramtil oil, rapeseed oil, rice bran oil, royle oil, sacha Inchi, safflower oil, salicornia oil, sesame oil, soybean oil, sunflower oil, tea seed oil, thistle oil, tigernut oil, tomato seed oil, tung oil, walnut oil, watermelon seed oil, wheat germ oil.

The base oil can also be a fatty acid, and preferred fatty acids include lauric acid, myristic acid, palmitic acid, caprylic acid, capric acid, stearic acid, caprioc acid, oleic acid, linoleic acid, arachidic acid, behenic acid, lignoceric acid, palmitoeic acid, linoleic acid, sapienic acid, alpha-liolenic acid, arachidonic acid, erusapentaenoic acid, erucic acid, docosahexaunoic acid, cerotic acid.

The pharmaceutically acceptable carrier of the present invention can be selected from the base oil as defined above or water or sugar or glycerol or a combination of the base oil as defined above and water and sugar and/or glycerol. Where the base oil is combined with a less hydrophobic phase, it is contemplated that the formulation can be a multi-phase formulation, an emulsion, a suspension, or other mixed phase formulation.

Therefore, it is preferred that contemplated compounds are included in a composition that is formulated with one or more non-toxic pharmaceutically acceptable carriers. Suitable pharmaceutical compositions are preferably formulated for oral administration in solid or liquid form, or for parenteral injection. Thus, it should be appreciated that pharmaceutical compositions according to the inventive subject matter may be administered to humans and other animals using various routes, including orally, rectally, parenterally, intraperitoneally, vaginally, or topically.

For example, suitable pharmaceutical compositions for injection preferably comprise pharmaceutically acceptable sterile aqueous or non-aqueous solutions, dispersions, emulsions, or suspensions, as well as sterile powders for reconstitution into sterile injectable solutions or dispersions prior to use. Examples of suitable aqueous and non-aqueous carriers, diluents, solvents, or vehicles include water, ethanol, polyols (e.g., glycerol, propylene glycol, polyethylene glycol, etc.), and suitable mixtures thereof, oils, and injectable organic esters (e.g., ethyl oleate). Contemplated compositions may also contain various inactive ingredients, including preservatives, wetting agents, emulsifying agents, and/or dispersing agents. Sterility may be ensured by inclusion of antibacterial and/or antifungal agents (e.g., paraben, phenol sorbic acid, chlorobutanol, etc.). Where appropriate, osmotically active agents may be included (e.g., sugars, sodium chloride, etc.).

Alternatively, contemplated compositions may be formulated into solid dosage forms for oral administration, and may therefore be capsules, tablets, pills, powders, and granules. In preferred solid dosage forms, contemplated compound are mixed with at least one of a pharmaceutically acceptable excipient or carrier (e.g., sodium citrate or dicalcium phosphate), a filler or extender (e.g., starch, lactose, sucrose, glucose, mannitol, or silicic acid), a binder (e.g., carboxymethylcellulose, alginates, gelatin, polyvinylpyrrolidone, sucrose, etc.), a humectant (e.g., glycerol), a disintegrating agent (e.g., agar-agar, calcium carbonate, potato or tapioca starch, alginic acid, certain silicates, or sodium carbonate), a solution retarding agent (e.g., paraffin), an absorption accelerator (e.g., quaternary ammonium compound), a wetting agents (e.g., cetyl alcohol and glycerol monostearate), and absorbents (e.g., kaolin, or bentonite clay), and a lubricant (e.g., talc, calcium stearate, magnesium stearate, solid polyethylene glycols, sodium lauryl sulfate).

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. Contemplated compositions may further be formulated to release the active ingredient(s) only, or preferentially, in a certain part of the intestinal tract, optionally, in a delayed manner. Examples of embedding compositions which can be used include polymeric substances and waxes. Contemplated compounds may also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, liquid dosage forms may contain inert diluents commonly used in the art (e.g., water, or other solvent, solubilizing agents), emulsifiers (e.g., ethyl alcohol, isopropyl alcohol, ethyl carbonate, ethyl acetate, benzyl alcohol, benzyl benzoate, propylene glycol, 1,3-butylene glycol, dimethyl formamide), oils (and in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions may also include adjuvants such as wetting agents, emulsifying and suspending agents, sweetening, flavoring, and perfuming agents.

Compositions according to the inventive subject matter can also be administered in form of liposomes, which may be unilamellar, oligolamellar, or polylamellar. Contemplated compositions in liposome form may further contain stabilizers, preservatives, excipients, etc. Preferred lipids for liposome formation include phospholipids and the phosphatidyl cholines (lecithins), both natural and synthetic. Methods to form liposomes are known in the art. See, for example, Prescott, Ed., Methods in Cell Biology, Volume XIV, Academic Press, New York, N.Y. (1976), p. 33 et seq.

The pharmaceutical compound of the inventive subject matter can be taken daily by a human patient at an effective amount from 0.1 mg to 50 mg or from 1 mg to 40 mg or from 5 mg to 30 mg or from 7 mg to 25 mg or from 8 mg to 20 mg or from 9 mg to 15 mg per kilogram body weight. Actual dosage levels of contemplated compounds in pharmaceutical compositions according to the inventive subject matter may be varied so as to obtain an amount of contemplated compound(s) that is effective to achieve the desired therapeutic response for a particular patient, composition, and mode of administration. Thus, the selected dosage level will depend upon various factors, including the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. If desired, the effective daily dose may be divided into multiple doses for purposes of administration, e.g., two to four separate doses per day.

In one preferred aspect, the pharmaceutical compound of the present invention is 4-hydroxy-2methyl-5-(propan-2-ylidene)cyclohex-3-ene-1-carbaldehyde, which may be enantiomerically pure, or a mixture of two or more stereoisomeric forms as depicted above. Consequently, a method of preparing pharmaceutical composition is also contemplated and may comprise: blending the compound of Formula 1 of the present invention at a temperature comprised preferably between 5° C. and 15° C. with a base oil in an amount of 5% to 20% by weight, preferably 10% to 15%, most preferably 11% to 14% to so obtain a mixture wherein the compound of the present invention is present in the composition in an amount effective for treatment and prevention of a cognitive, neurodegenerative or neuronal disorder or disease. As noted before, suitable diseases include chronic neurodegenerative conditions including dementias such as Alzheimer's disease, memory loss, attention deficit symptoms associated with Alzheimer's disease, diffuse Lewy body type Alzheimer's disease, mild cognitive impairment, Hereditary Cerebral Haemorrhage with Amyloidosis of the Dutch-Type, [beta]-amyloid angiopathy and cerebral bleeding such as cerebral bleeding due to solitary cerebral amyloid angiopathy, prion infections, degenerative dementias, including dementias of mixed vascular and degenerative origin, frontotemporal dementia, pre-senile dementia, senile dementia, parkinsonian disorders such as Parkinson's disease (PD), subacute sclerosing panencephalitic parkinsonism, postencephalitic parkinsonism, pugilistic encephalitis, guam parkinsonism-dementia complex, Pick's disease, multiple system atrophy (MSA), progressive supranuclear palsy (PSP), and corticobasal degeneration (CBD), Down syndrome, Lewy body disease, Huntington's Disease, amyotrophic lateral sclerosis, multiple sclerosis and neurotraumatic diseases such as acute stroke, epilepsy, promotion of functional recovery post stroke, ischaemia, brain injury, especially traumatic brain injury and neuroinflammation.

The present disclosure also concerns a method for treating a subject suffering from a cognitive, neurodegenerative or neuronal disorder or disease, comprising the step of: administering a therapeutically effective amount of the pharmaceutical composition comprising a compounds according to Formula A with or without any pharmaceutically acceptable carrier. In some aspects, the compound according to Formula A has the structure according to Formula 1. The compound can be a mixture of stereoisomers or a single stereoisomer as discussed above. The cognitive, neurodegenerative or neuronal disorder or disease being the Alzheimer's disease. The administration can be made either orally, or topically, or parentally, or by rectal route, or by injection, or by inhalation, or by a patch.

The present disclosure concerns also a method for treatment and prevention of a cognitive, neurodegenerative or neuronal disorder or disease, said disorder or disease being the Alzheimer's disease, said method for treatment comprises the following step: administering a therapeutically effective amount of the pharmaceutical composition comprising a compound according to Formula A together with an amount of a base oil either orally, or topically, or parentally, or by rectal route, or by injection, or by inhalation, or by a patch. It should be appreciated that compositions comprising the compound of Formula A and base oil can be used for the method of preparing pharmaceutical composition of the present invention and in the method for treatment and prevention of a cognitive, neurodegenerative or neuronal disorder or disease in the amounts described herein. In typical aspects, the compound according to Formula A has a structure according to Formula 1, or a mixture of its stereoisomers (see Formulas 2-5) or a single stereoisomer as described above.

Still further, it is contemplated that the compounds and formulations presented herein may be used in diagnosis or visualization of diseased neuronal tissues, especially tissues associated with a cognitive, neurodegenerative or neuronal disorder or disease. For example, a diagnostic composition is contemplated that comprises a compound according to Formula A and a PET- or SPECT detectable label. Most preferred labels include $^{18}F$ and $^{11}C$. In other contemplated embodiments, a diagnostic composition comprises a compound according to Formula 1 and a PET- or SPECT detectable label. It should be appreciated that the compound can comprise a mixture of stereoisomers (see Formulas 2-5) or a single isolated stereoisomer as described above.

In typical aspects, a method of manufacture and galenics is contemplated. The purity of the components preferably has to be ≥99%, which is verified before the formulation process by gas chromatography/mass spectrometry. The preferred temperature of manufacturing and storage of the composition is between 5 and 15 degrees Celsius.

Contemplated compounds of the inventive subject matter can be blended to a pharmaceutically acceptable carrier to form a mixture. Depending on the type of application, the ratio between the composition of the present invention and the pharmaceutically acceptable carrier can range from 1% to 90%, from 10% to 80%, from 20% to 70%, from 30% to 60%, from 40% to 50%, where 20% is the most common ratio used for practical medical applications. In another aspect, the method for manufacturing a contemplated composition comprises the following steps: blending the compound of Formula A at a temperature comprised preferably between 5 and 15° C. with a base oil at a rate of 5% to 20% by weight, preferably 10% to 15%, most preferably 11% to 14%. Other working ranges are 5% to 15% by weight, 5% to 14% by weight, 5% to 10% by weight, 5% to 11% by weight, 10% to 20% by weight, 10% to 15% by weight, 10% to 14% by weight, 10% to 11% by weight, 11% to 15% by weight, 12% to 13% by weight, to obtain a mixture. It is contemplated that the compound according to Formula A has the structure according to Formula 1. Additionally, the compound can be a mixture of stereoisomers (e.g., Formulas 2-5) or an isolated stereoisomer.

Exemplary Synthesis of Contemplated Compounds

It should generally be appreciated that contemplated compounds (e.g., Formula 1) may be prepared from various precursors following numerous routes (either individually, serially, or in parallel fashion, or even using combinatorial synthetic strategies). For example, the compound of Formula 1, including salts thereof, can be prepared using known organic synthesis techniques and can be synthesized according to any of numerous possible synthesis routes. Thus, the following is therefore only provided as exemplary guidance for starting materials, conditions, and synthesis of selected compounds.

The experimental example, which follows, is illustrative and does not restrict the scope of the invention:

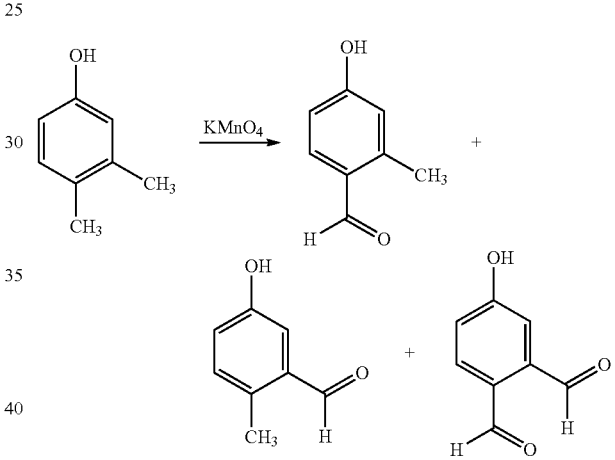

The production of the compound of Formula 1 can be performed in two steps with a first step comprising partial oxidation of a precursor compound (here: 3,4-Xylenol) using an oxidizing agent (here: $KMnO_4$) as depicted above, and a second step in which the intermediate is alkylated to the desired compound as explained and depicted below. It should be noted that after a relatively short time and at room temperature, oxidation using permanganate is partial, and that each of the methyl groups of 3,4-Xylenol can be oxidized to the corresponding aldehyde.

After this first step, the alkylation can be done with the reaction mixture after dilution in PBS buffer in a Friedel Craft-type alkylation that introduces the propene group using 2-Chloropropene. Depending on the nature of the group attached on the ring, the alkylation is oriented on ortho, meta or para. This is typically governed by the ability of the substituents to stabilize the positive charge of Wheland Complex that appears on the ring after nucleophilic attack. For example, substituents like NH2, NHR, NR2, OH, OR are ortho, para directing when NO2, CF3, NR3+, COOH, COOR, COR, or alkyl group are meta directing (R can be hydrogen).

The compound of Formula 1 is formed by the ring reduction allowed by the acid chloride produced during alkylation. Thus, PBS is added in combination with glycerol to stop the reaction by dilution which decreases their concentration. The PBS buffer is also used to buffer the solution to avoid complete reduction. The mechanism is shown below:

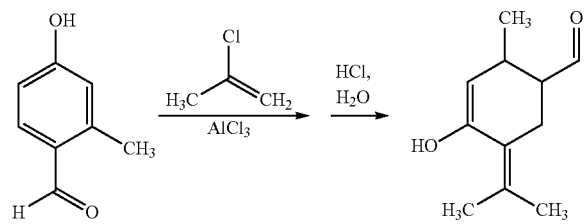

Figure 1B:
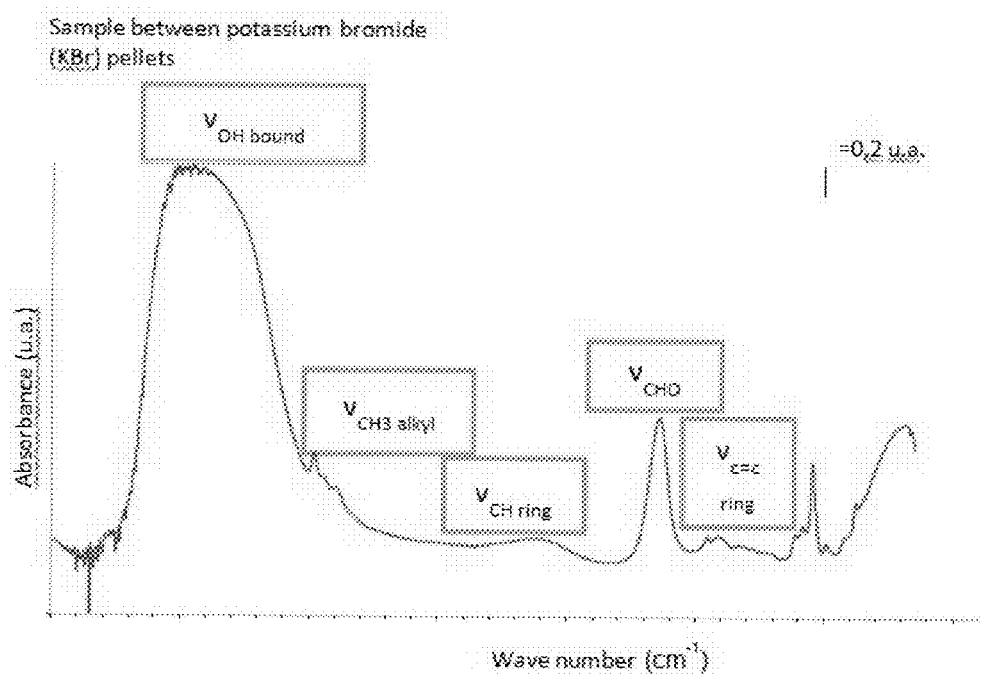
FIG. 1B is an infrared spectrometry analysis of (1R,2R) and (1S,2S) trans isomers of Formula 1.

The compound in this final mixture was identified using gas chromatography coupled to mass spectrometry analysis (GC-MS) shown in FIG. 1A. As shown, the products are in small quantities about 0.028% of Trans isomers and 0.018% CIS isomers comparing to the toluene's spike: Trans: 80% (1R,2R)-20% (1S;2S) and CIS: 50% (1S,2R)-60% (1R,2S) (see Table 1). The final mixtures containing the compound having all 4 stereoisomers in their relative amounts was used in the observational studies on the volunteers as described below. The final mixture is now void of any harmful reactives and the remaining reactives such as 3,4 Xylenol are unharmful in such small doses (e.g., LD50 of 3,4 Xylenol is 900 mg/kg weight). Infrared and Raman spectroscopies were performed to verify the functional groups present in the major trans product formed by the reaction disclosed above in FIGS. 1B-1C.

TABLE 1

| quantities | Isomers | | | |
|---|---|---|---|---|
| | Trans (1R, 2R) | Trans (1S, 2S) | Cis (1S, 2R) | Cis (1R, 2S) |
| Total Quantity (%) | 0.028% | | 0.018% | |
| Individual (%) | 80% | 20% | 50% | 50% |

TABLE 2

| Reagents | Quantities |
|---|---|
| benzylic alcohol | |
| 3,4 xylenol | 250 g |
| 2-chloropropen | 5 g |
| Ethanol 95% | |
| Ether 5% | |
| KMnO$_4$ | 25 g |
| AlCl$_3$ | 5 g |
| PBS 10 X | 6 × 500 ml |
| Tablets PBS | 100 TAB |
| Glycerol | 1 liter |
| Oil | 0.75 liter |

TABLE 3

| A7: reagents | Reaction 44.4 ml final volume |
|---|---|
| Ethanol 95% ether 5% + 3,4 xylenol | 10 ml + 1.2 mg |
| KMnO$_4$ | 12.5 uL |
| 2-chloropropen + AlCl$_3$ | 1.5 ml + 8.4 mg |
| PBS 1X | qsp 40 ml |
| Glycerol | 4.4 ml |

Tables 2 and 3 show reagents involved in the synthesis of the compound mixture having Formula 1. Reaction in a final volume of 44.4 ml: (i) dissolve a quantity of 1.2 mg xylenol into a 10 mL solvent of ethanol volume of 95%, ether 5% so that the xylenol is at 1M pH control, (ii) add a volume of KMnO4/0.2M so that its final concentration is 0.5 mM and incubate at TR during 15 minutes PH control, (iii) add an equal volume of 2-chloropropene and AlCl3 and incubate 5 minutes at 30° C. (note that equal volume is with respect to the volume produced after step (ii)), and (iv) add a mixture of PBS and glycerol to obtain a final volume of 44 ml while measuring the pH, putting parafilm and conserving the tube at −20° C. As discussed in this paragraph, pH control means to add PBS until the pH of 7.4 (physiological condition) is reached. It should be appreciated that PBS is added until physiological condition (pH=7.4) to allow for purification (i.e., clean up impurities).

As mentioned above, the PBS (phosphate buffered saline) buffer has two roles. First, it will contribute to buffer the solution mixture in order to increase the pH, from acid (about 3 in the reaction) to neutral (pH=7.4) so to make inappropriately adverse reactions such as ring reduction in acidic solution. Secondly, the dilution made by adding PBS will lead to decreasing reagent concentrations in order to stop reaction. Glycerol is added to help increase the viscosity of the solution mixture and help the reaction to stop. As it is known, glycerol is a cryo-protective molecule so it prevents freeze damage.

Selected Experiments Using Contemplated Compositions

The progression of Alzheimer's disease can be divided into seven internationally recognized stages. The recognized stages are useful for understanding the various experiments described below.

Stage 1: No impairment (normal function). The person does not experience any memory problems. An interview with a medical professional does not show any evidence of symptoms.

Stage 2: Very mild cognitive decline (may be normal age-related changes or earliest signs of Alzheimer's disease). The person may feel as if he or she is having memory lapses forgetting familiar words or the location of everyday objects. But no symptoms can be detected during a medical examination or by friends, family or co-workers.

Stage 3: Mild cognitive decline (early-stage Alzheimer's can be diagnosed in some, but not all, individuals with these symptoms). Friends, family or co-workers begin to notice difficulties. During a detailed medical interview, doctors may be able to detect problems in memory or concentration. Common stage 3 difficulties include: noticeable problems coming up with the right word or name. Trouble remembering names when introduced to new people having noticeably greater difficulty performing tasks in social or work settings, forgetting material that one has just read losing or misplacing a valuable object, increasing trouble with planning or organizing. Lasts about 2 years.

Stage 4: Moderate cognitive decline (mild or early-stage Alzheimer's disease). At this point, a careful medical interview should be able to detect clear-cut problems in several areas: forgetfulness of recent events, impaired ability to perform challenging mental arithmetic (for example, counting backward from 100 by 7 s), greater difficulty performing complex tasks, such as planning dinner for guests, paying bills or managing finances, forgetfulness about one's own personal history, becoming moody or withdrawn, especially in socially or mentally challenging situations. Lasts about 2 years.

Stage 5: Moderately severe cognitive decline (Moderate or mid-stage Alzheimer's disease). Gaps in memory and thinking are noticeable, and individuals begin to need help with day-to-day activities. At this stage, those with Alzheimer's may: be unable to recall their own address or telephone number or the high school or college from which they graduated, become confused about where they are or what day it is, have trouble with less challenging mental arithmetic; such as counting backward from 40 by subtracting 4 s or from 20 by 2 s, need help choosing proper clothing for the season or the occasion, still remember significant details about themselves and their family, still require no assistance with eating or using the toilet. Lasts about 1 year.

Stage 6: Severe cognitive decline (moderately severe or mid-stage Alzheimer's disease). Memory continues to worsen, personality changes may take place and individuals need extensive help with daily activities. At this stage, individuals may: lose awareness of recent experiences as well as of their surroundings, remember their own name but have difficulty with their personal history, distinguish familiar and unfamiliar faces but have trouble remembering the name of a spouse or caregiver, need help dressing properly and may, without supervision, make mistakes such as putting pajamas over daytime clothes or shoes on the wrong feet, experience major changes in sleep patterns, sleeping during the day and becoming restless at night, need help handling details of toileting (for example, flushing the toilet, wiping or disposing of tissue properly), have increasingly frequent trouble controlling their bladder or bowels, experience major personality and behavioral changes, including suspiciousness and delusions (such as believing that their caregiver is an impostor) or compulsive, repetitive behavior like hand-wringing or tissue shredding, tend to wander or become lost. Lasts about 1 year.

Stage 7: Very severe cognitive decline (Severe or late-stage Alzheimer's disease). In the final stage of this disease, individuals lose the ability to respond to their environment, to carry on a conversation and, eventually, to control movement. They may still say words or phrases. At this stage, individuals need help with much of their daily personal care, including eating or using the toilet. They may also lose the ability to smile, to sit without support and to hold their heads up. Reflexes become abnormal. Muscles grow rigid. Swallowing impaired. Lasts about 1 year.

Experimental Data 1

Patient JH01

A 78 year old stage 6 Alzheimer confirmed patient (JH01) was diagnosed with Alzheimer's disease. The patient was tested using the internationally recognized mini-mental state examination (MMSE) or Folstein test, a brief 30-point questionnaire test that is used to screen for cognitive impairment. The patient had a declining Mini-Mental State Examination (MMSE) score of 2 out of 30 at the beginning of the study (day 0).

The patient was given over 6 months 3 times a day 500 mg of a mixture of 80% by weight of Olive oil with 20% by weight of the glycerol-containing raw reaction mixture of the present invention. After one month, the care takers started to notice a general improved mental state of the patient. After two months, the patient started to try to dress himself and started to ask about lunch and dinner times, which he never did in the past. After three months, the patient could hold very small conversations with the care takers that made sense. He started to refer to certain events of the past.

After three months, a new MMSE was taken. Although the score was still very low, 8 out of 30 the improvement was considerable. After 6 months, the patient mental state had improved considerably. Although he could not answer obvious questions like which province he was, this could be due to the fact that these questions were never asked in the past and there was no direct reference to them as then patient lived for years in a rather isolated environment. He could however answer direct questions to very short term events.

After 6 months, the MMSE questions on these short term issues improved considerably and the score reached 13 out of 30 as shown in FIG. 2. This indicates that the patient could function as good as patient in stage 4 or less. The unexpected improvement in total points over 6 months was 11 points on a scale of 30, which shows a surprising and unexpected improvement.

From FIG. 2 it is apparent that the unexpected and surprising effect is that the patient gained 11 points 6 months after having taken 3 times a day the pharmaceutical composition of the present invention.

Experimental Data 2

Patient AA7-003

A 79 year old, stage 6 Alzheimer confirmed patient was administered 200 mg of the glycerol-containing raw reaction mixture of the present invention mixed with 800 mg olive oil 3 times a day over a period of 6 months.

The patient was tested using the internationally recognized mini-mental state examination (MMSE) or Folstein test, a brief 30-point questionnaire test that is used to screen for cognitive impairment. It is commonly used in medicine to screen for dementia, such as Alzheimer's disease. It is also used to estimate the severity of cognitive impairment and to follow the course of cognitive changes in an individual over time, thus making it an effective way to document an individual's response to treatment at which he scored 6 out of 30 at the beginning of the study (day 0).

The care taker was also questioned and the observations recorded using the internationally recognized Barthel Index as shown in FIG. 3, which consists of 10 items that measure a person's daily functioning specifically the activities of daily living and mobility. The items include feeding, moving from wheelchair to bed and return, grooming, transferring to and from a toilet, bathing, walking on level surface, going up and down stairs, dressing, continence of bowels and bladder.

The assessment can be used to determine a baseline level of functioning and can be used to monitor improvement in activities of daily living over time. The items are weighted according to a scheme developed by the authors. The person receives a score based on whether they have received help while doing the task. The scores for each of the items are summed to create a total score. The higher the score the more "independent" the person. Independence means that the person needs no assistance at any part of the task. If a person does about 50% independently then the "middle" score would apply. The patient scored 50 out of 100 at the base line (see FIG. 3).

During the treatment the patient gradually regained cognitive ability and his daily functioning improved as well. The patient experienced several periods of anxiety, which are contributed to the confusion, linked to the awakening of his cognitive abilities. The patient was given a controlled treatment of natural tranquilizers. After 3 months the periods of anxiety subsided indicating that he passed the critical reversal of the transition of stage 6 to stage 5.

After 6 months the Mini mental state examination (MMSE) score had increased with 9 points giving him a score of 15 out of 30 as shown in FIG. 4, a score that is close to the score of a 5-6 stage patient. This shows a surprising and unexpected improvement. The Barthel Index of the same patient also increased considerably: 50 points (see FIG. 3). This also shows a surprising and unexpected improvement. These experimental data indicate that the patient could function as good as a patient in stage 4 or less.

From FIG. 4 it is apparent that the unexpected and surprising effect is that the patient gained 9 points 6 months after having taken the pharmaceutical composition of the present invention. From FIG. 3 it is apparent that the unexpected and surprising effect is that the patient gained 50 points 6 months after having taken the pharmaceutical composition of the present invention.

Experimental Data 3

We also included a Placebo group who were given aromatized olive oil and a control group of normal healthy patients who were given nothing. In total there are 2 subjects enrolled in each of the 3 groups. The test performed is the Short term Memory Recovery Test or SMIT and it is specially designed to quantify the amount of actions, subjects or objects that can be retained by each subject in an interval of 48 hours. The subject is told a short story using day-to-day actions and subjects. The subject is then requested to repeat the story, gaining points on the correctness and completeness of the information. When the subject misses a step, the interrogator will ask an intermediate question. Without the intermediate question the subjects receives 2 times the points with aid only one point. If the story is not correct or forgotten 0 points are awarded.

This test was performed 3 times starting with one test as a base line, one test after 30 months and one test after 60 months. Each time with 48 hours between telling the story and the interrogation. It is expected that a healthy person's answer will improve with each session. For example, the healthy person might have forgotten the name of the hotel the first time, but the will recall the name of the second or third time.

Typically, Alzheimer's patients of this stage (stage 4-5 Alzheimer's patients) do not improve over the span of the multiple tests. On some occasions the Neurotransmitters will access the memory, but most typically, the same story will be lost at the interview. With the aid of intermediate questions some access can be triggered.

Patients were given capsules 3 times a day of 500 mg with 400 mg olive oil and 100 mg of the raw mixture as synthesized above (3,4-Xylenol, 2-chloropropen, ethanol, esther, glycerol), which contains the compound of Formula 1 and its stereoisomers at 0.03 mg Trans(1R,2R), 0,006 mg Trans(1S,2S), 0.01 tmg Cis(1S,2R) and 0.01 mg Cis(1R,2S). The Placebo groups were given capsules of 500 mg with 0.5 mg of Geraniol, which is a flavoring agent. For the period of 60 months none of the groups took any special medication that would interfere with the study.

As shown in FIG. 5, the SMIT test showed that the Placebo group scored minimal in all 3 tests only 5, 3 and 3. The Active group however scored very low at the beginning (6) but gradually improved over the course of 60 months to a score of 28, which is still well below the normal, but indicates a strong improvement versus placebo confirming the surprising effect of the initial Late stage Alzheimer patients.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Moreover, and unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure all terms should be interpreted in the broadest possible manner consistent with the context. In particular the terms "comprises" and "comprising" should be interpreted as referring to the elements, components, or steps in a non-exclusive manner, indicating that the referenced elements, components, or steps can be present, or utilized, or combined with other elements, components, or steps that are not expressly referenced.

What is claimed is:

1. A compound having a structure according to Formula A

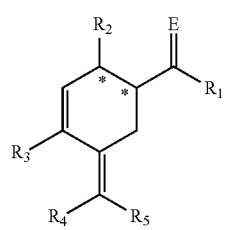

Formula A wherein $R_1$ is hydrogen or lower alkyl;
wherein $R_2$ is lower alkyl;
wherein $R_3$ is OH or SH;
wherein $R_4$ and $R_5$ are lower alkyl; and
wherein $R_1$, $R_2$, $R_3$, $R_4$, and $R_5$ are independently, optionally labelled with $^{18}F$ or $^{11}C$; and
E is O or S.

2. The compound of claim 1 having a structure according to Formula 2

Formula 2

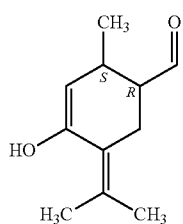

3. The compound of claim 1 having a structure according to Formula 3

Formula 3

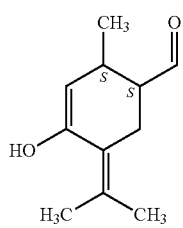

4. The compound of claim 1 having a structure according to Formula 4

Formula 4

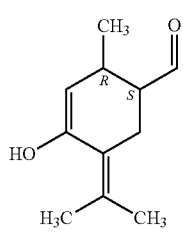

5. The compound of claim 1 having a structure according to Formula 5

Formula 5

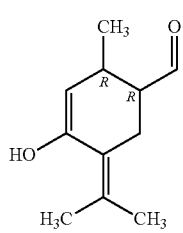

6. The compound of claim 1, wherein the compound is a mixture of two from the group consisting of

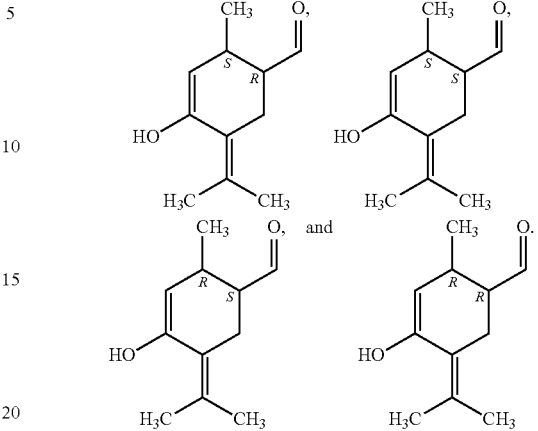

7. The compound of claim 1, wherein the compound is a mixture of three from the group consisting of

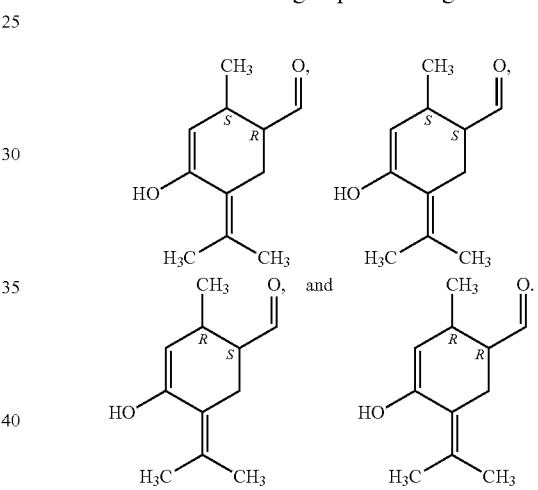

8. A pharmaceutical composition, comprising a compound according to claim 1, or a salt thereof, and a pharmaceutically acceptable carrier.

9. The pharmaceutical composition of claim 8, wherein the compound is present in the pharmaceutical composition in an amount effective to treat Alzheimer's disease.

10. A method of treating Alzheimer's disease in a subject, comprising administering a compound according to claim 1 at a concentration effective to treat Alzheimer's disease in said subject.

* * * * *